(12) United States Patent
Deutsch

(10) Patent No.: US 7,179,611 B2
(45) Date of Patent: Feb. 20, 2007

(54) **MONO-SPECIFIC POLYCLONAL ANTIBODIES AND METHODS FOR DETECTING *CLOSTRIDIUM DIFFICILE* TOXIN A**

(75) Inventor: John William Deutsch, Marietta, GA (US)

(73) Assignee: BD Lee Laboratories, Grayson, GA (US)

(*) Notice: Subject to any disclaimer, the term of this patent is extended or adjusted under 35 U.S.C. 154(b) by 602 days.

(21) Appl. No.: 10/224,752

(22) Filed: Aug. 20, 2002

(65) Prior Publication Data

US 2003/0018170 A1    Jan. 23, 2003

Related U.S. Application Data

(63) Continuation-in-part of application No. 08/797,959, filed on Feb. 10, 1997.

(51) Int. Cl.
*G01N 33/554* (2006.01)
*C07K 1/22* (2006.01)

(52) U.S. Cl. .................. 435/7.32; 530/350; 435/7.2; 436/533

(58) Field of Classification Search ............ 424/184.1, 424/93.1, 130.1, 167.1, 150.1, 164.1; 530/300, 530/389.1; 435/7.32; 536/531, 532, 808, 536/811, 518
See application file for complete search history.

(56) References Cited

U.S. PATENT DOCUMENTS

| | | | |
|---|---|---|---|
| 4,530,833 A | 7/1985 | Wilkins et al. ............. 530/350 |
| 4,533,630 A | 8/1985 | Wilkins et al. ................ 435/7 |
| 4,713,240 A * | 12/1987 | Wilkins et al. .......... 424/239.1 |
| 4,863,852 A | 9/1989 | Wilkins et al. ............ 435/7.25 |
| 4,879,218 A * | 11/1989 | Wilkins et al. ............ 435/7.32 |
| 4,937,201 A * | 6/1990 | Ueno et al. ................. 436/533 |
| 5,071,759 A | 12/1991 | Rothman et al. ........ 530/388.4 |
| 5,098,826 A | 3/1992 | Wilkins et al. ............ 435/7.32 |
| 5,231,003 A | 7/1993 | Coughlin et al. .......... 435/7.32 |
| 5,736,139 A | 4/1998 | Kink et al. ............... 424/164.1 |
| 5,965,375 A | 10/1999 | Valkirs ....................... 435/7.2 |
| 6,290,960 B1 * | 9/2001 | Kink et al. ............... 424/164.1 |
| 6,573,003 B2 * | 6/2003 | Williams et al. ......... 424/190.1 |
| 6,613,329 B1 * | 9/2003 | Kink et al. ............... 424/164.1 |

FOREIGN PATENT DOCUMENTS

| | | |
|---|---|---|
| EP | 0 153 519 | 4/1985 |
| EP | XP-00217981-4 | 6/1988 |
| WO | WO 96/30494 | 10/1996 |
| WO | WO 2004/017899 | 3/2004 |

OTHER PUBLICATIONS

Renner, 1994, reference of record.*
Knoop et al, 1993, reference of record.*
Lyerly et al 1983, Journal of Clinical Microbiology, vol. 17(1), pp. 72-78, Jan., reference of record.*
Kamiya et al (1986), reference of record.*
Rodkey, LS, Comparative properties of polyclonal and monoclonal antiboides, Chapter 8, from Methods in Molecular Biology, vol. 51, pp. 139-150, 1995.*
Ramamurthy, T et al, Indian Journal of Medical Research, Jul. 1996, vol. 104, pp. 125-128, Comparison of the sensitivity and specificity of a polyclonal versus monoclonal capture antibody based Bead ELISA for direct detection cholera toxin from stool.*
Campbell, Ailsa M. Monoclonal antibody and immunosensor technology, 1991, Laboratory Techniques in Biochemistry and Molecular Biology, vol. 23, pp. v-49.*
Renner reference of record.*
Knoop et al (1993) reference of record.*
Kamiya et al (1986) reference of record.*
Lyerly et al (1983) reference of record.*
Kamiya, S. et al., Production of monoclonal antibody to *Clostridium difficile* toxin A which neutralises enterotoxicity but not haemagglutination activity, FEMS Microbiology Letters, 1991, vol. 81, pp. 311-316, especially p. 314 and entire document.
Knoop, FC. et al., *Clostridium difficle:* clinical disease and diagnosis, Clinical Microbiology Reviews, Jul. 1993, vol. 6. No. 3, pp. 251-265, especially p. 256, cols. 1-2 and entire document.
Renner (1994). Comm. in Clinical Cytometry. vol. 18, pp. 103-108.
Banno et al. Mar.-Apr. 1984. Review of Infectious Disease. vol. 6. Supplement 1. pp. S11-S20.
Lyerly et al. Jan. 1985. J. Clinical Microbiology. vol. 21(1). pp. 12-14.
XP-002179812, 1988, Europe.
XP-002179813, Oct. 1986, Europe.
XP-001030519, Jan. 1985, Europe.
Wilkins in view of Kamiya et al. Microbiology and Immunology, vol. 3(2). 1986.
Muldrow, L.L. et al. (1987) FEBS Letters. vol. 213(2). pp. 249-253.
Wren. B.W. et al. Dec. 1987. FEBS Letters. vol. 225(1.2). pp. 82-86.
Ngo. et al. (1990) J. of Chrom.. vol. 510. pp. 281-291.
Domen et al. (1990). J. Chromatography. vol. 510. pp. 293-303.
Campbell. A.M. (1991). Laboratory Techniques in Biochemistry and Molecular Biology. Elsevier Publishers. Chapter 1. pp. 1-41.
Frey et al. Jun. 1992. Infect. Immun.. vol. 60(6). pp. 2488-2492.
Doern. et al. Aug. 1992. J. Clin. Microbiol.. vol. 30(8). pp. 2042-2046.

* cited by examiner

Primary Examiner—Mark Navarro
Assistant Examiner—Ginny Allen Portner
(74) Attorney, Agent, or Firm—Thomas, Kayden, Horstemeyer & Risley

(57) ABSTRACT

A method is provided for the purification of *Clostridium difficile* Toxin A antigen comprising reacting impure Toxin A with immobilized mono-specific polyclonal antibodies. The polyclonal antibodies are coupled to a hydrazide group containing matrix such as hydrazide activated agarose gel. The immobilized antibody is specific for Toxin A and will greatly purify Toxin A from a Toxin A containing solution. Antibodies raised to Toxin A purified according to the method are of higher activity than antibodies produced from prior art purified Toxin A.

3 Claims, 3 Drawing Sheets

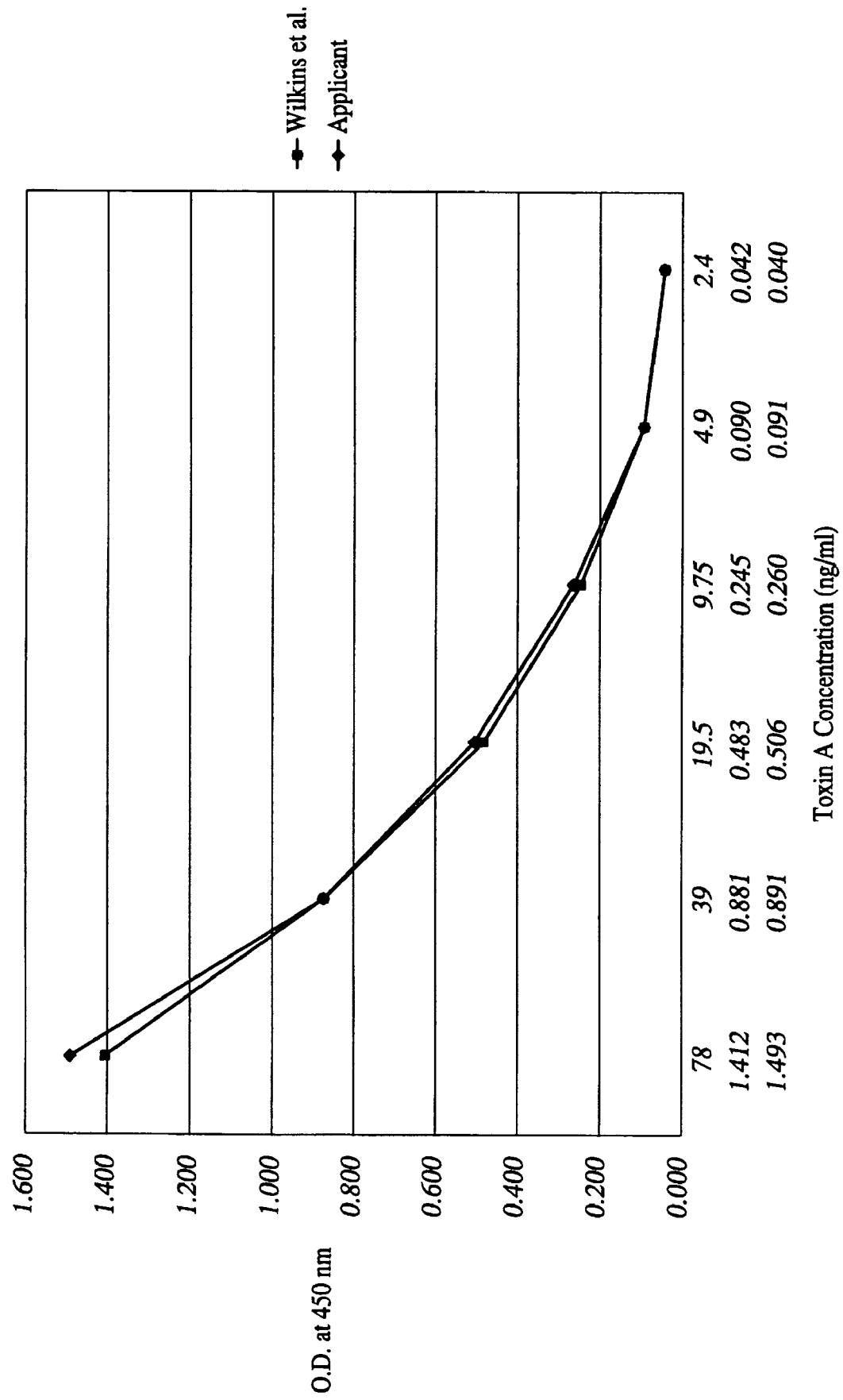

FIG.2 Comparision Mab vs Pab xtoxin A

- Mab xtoxin A
- Pab xtoxin A Ab

O.D. at 450 nm

| Toxin A Concentration (ng/ml) | 78 | 39 | 19.5 | 9.75 | 4.8 | 2.4 |
|---|---|---|---|---|---|---|
| Mab | 0.486 | 0.342 | 0.145 | 0.061 | -0.002 | 0.011 |
| Pab | 1.179 | 0.715 | 0.446 | 0.218 | 0.103 | 0.025 |

FIG.3

Absorbance Values

| | | Antibody Dilutions: | 1:160K | 1:320K | 1:640K | Blank | Endpoint ELISA Titer |
|---|---|---|---|---|---|---|---|
| Test 1 | Test Lot # | 1 | 0.363 | 0.251 | 0.165 | 0.081 | 1:640K |
| | Reference Lot # | 1 | 0.401 | 0.285 | 0.231 | 0.198 | 1:640K |
| Test 2 | Test Lot # | 2 | 0.408 | 0.366 | 0.318 | 0.277 | 1:640K |
| | Reference Lot # | 1 | 0.492 | 0.362 | 0.299 | 0.269 | 1:640K |
| Test 3 | Test Lot # | 3 | 0.221 | 0.191 | 0.184 | 0.141 | 1:640K |
| | Reference Lot # | 1 | 0.226 | 0.193 | 0.191 | 0.142 | 1:640K |
| Test 4 | Test Lot # | 4 | 0.714 | 0.613 | 0.534 | 0.267 | 1:640K |
| | Reference Lot # | 1 | 0.471 | 0.410 | 0.425 | 0.267 | 1:640K |
| Test 5 | Test Lot # | 5 | 0.463 | 0.366 | 0.260 | 0.192 | 1:640K |
| | Reference Lot # | 1 | 0.440 | 0.410 | 0.250 | 0.183 | 1:640K |
| Test 6 | Test Lot # | 6 | 0.402 | 0.202 | 0.091 | 0.131 | 1:320K |
| | Reference Lot # | 2 | 0.441 | 0.215 | 0.091 | 0.187 | 1:320K |
| Test 7 | Test Lot # | 7 | 0.495 | 0.338 | 0.250 | 0.220 | 1:640K |
| | Reference Lot # | 3 | 0.517 | 0.369 | 0.250 | 0.214 | 1:640K |
| Test 8 | Test Lot # | 8 | 0.399 | 0.265 | 0.182 | 0.103 | 1:640K |
| | Reference Lot # | 4 | 0.364 | 0.235 | 0.166 | 0.105 | 1:640K |
| Test 9 | Test Lot # | 9 | 0.478 | 0.245 | 0.132 | 0.103 | 1:640K |
| | Reference Lot # | 5 | 0.350 | 0.128 | 0.060 | 0.103 | 1:320K |

MONO-SPECIFIC POLYCLONAL ANTIBODIES AND METHODS FOR DETECTING *CLOSTRIDIUM DIFFICILE* TOXIN A

CROSS-REFERENCE TO RELATED APPLICATION

This application claims priority to and benefit of copending U.S. utility patent application entitled, "Method of Purification of *C. Difficile* Toxin A and Production of Mono-Specific Antibodies," filed on Feb. 10, 1997, and accorded U.S. Ser. No. 08/797,959.

FIELD OF THE INVENTION

The invention relates generally to the production and purification of *Clostridium difficile* Toxin A. More particularly, the invention relates to purified Toxin A and its use in preparing antibodies.

BACKGROUND OF THE INVENTION

*Clostridium difficile* produces an assortment of gastrointestinal diseases in humans and animals ranging from mild diarrhea to life threatening pseudomembranous colitis. It is widely accepted that *C. difficile* causes pseudomembranous colitis in humans as a result of the elimination of the normal flora of the colon by antibiotic usage and subsequent growth of this toxin producing bacterium. The disease usually occurs in institutionalized and/or hospitalized patients where it causes a massive diarrhea with extensive inflammation of the colon. Mortality rates as high as 44% have been reported. Treatment of the disease is possible but relies on a proper diagnosis which may be accomplished by establishing the presence of the causation organism and demonstrating the characteristic lesions in the colon.

*C. difficile* produces two toxins, designated Toxin A and Toxin B, that are cytotoxic for tissue cultured mammalian cells. In addition to its cytotoxicity, Toxin A also possesses enterotoxin activity. Toxin A causes an accumulation of fluid in the intestine loops and causes extensive damage to the gut mucosa. Although both toxins are typically produced during disease, the principle laboratory diagnostic methods for detection of *C. difficile* have been directed towards detection of Toxin A. For example, a commercial latex test for the presence of Toxin A was marketed by Marion Scientific, a division of Marion Laboratories, Inc. of Kansas City, Mo. This commercial test was, unfortunately, found by subsequent researchers to be non-specific for Toxin A. See Lyerly et al., *J. Clin. Micro*, 23: 622–623 (1986).

One method for detecting pathogenic *C. difficile* involves the culture of human feces, which requires specialized facilities for long periods of incubation and which has the disadvantage of interference by non-pathogenic *C. difficile* strains. Another method for detecting Toxin B, but which does not work well for detecting Toxin A, is cytotoxicity assays using tissue culture cells. Because Toxin A is a much less potent cytotoxin it is more difficult to detect in tissue culture assays.

Other methods developed for Toxin A detection have been based on the use of specific antibodies to Toxin A. These methods include the enzyme-linked immunosorbent assay (ELISA) as taught by Lyerly et al., *J. Clin. Micro.*, 17: 72–78 (1983) and Laughton et al, *J. Infect. Dis.*, 149: 781–788 (1984). Lyerly et al reported detection of Toxin A at 1 ng (5 ng/ml) quantities while Laughton et al. reported detection at 0.1 ng (1.0 ng/ml) levels. An ELISA assay using a monoclonal antibody to Toxin A was reported by Lyerly et al., *J. Clin. Micro*, 21: 12–14 (1985), which could detect 4 ng (0.02 µg/ml) of Toxin A. This detection level is usually adequate to detect the toxin in stool samples from patients with *C. difficile*-related diarrhea. Another antibody dependent test is the Latex Agglutination Test (LAT) wherein the antibody is immobilized on latex beads and agglutination of said beads by soluble Toxin A is visualized.

U.S. Pat. No. 4,530,833 to Wilkins et al. teaches a method of purifying Toxin A from cell culture supernatant which comprises an ion-exchange chromatography step followed by isoelectric precipitation. The patent teaches that purified Toxin A is achieved by adjusting the pH and molarity of a solution of impure Toxin A to, preferably, 5.5 and 0.01, respectively. One disadvantage of using isoelectric precipitation for protein purification is that other proteins with similar properties as the desired protein aggregate and coprecipitate with the desired protein to form the isoelectric precipitate. Thus, the precipitate must be washed by resuspension and recentrifugation. This results in loss of the desired protein. In addition, the process prior to and including the precipitation step must be very carefully controlled to control the precipitation step. If the fractions from the ion-exchange column are not carefully and consistently pooled, more or less proteins will co-precipitate with the Toxin A.

Another disadvantage of isoelectric precipitation with respect to purification of Toxin A is that denaturation of Toxin A may result if high speeds are used to pellet the precipitated protein. Thus, the protein will not be active in immunoassays or when used as an immunogen for antibody production. Isoelectric precipitation of proteins may also cause changes in the tertiary structure of the protein. In particular, Toxin A is an extremely hydrophobic protein and its exposure to a low ionic strength buffer for several wash steps can result in its partial denaturation.

Another method of Toxin A purification is taught in U.S. Pat. No. 5,098,826 to Wilkins et al. This method comprises contacting an impure solution of Toxin A with an immobilized reagent containing one or more of the terminal non-reducing structures characteristic of any of the human antigens X, Y, or I. These structures are known to be polysaccharides, and they can be immobilized by binding them to an insoluble matrix, e.g., silica gel, agarose, latex beads, or the like. The Toxin A binds to the immobilized reagent and is then eluted from the reagent in a more pure form. This method requires one of the antigens X, Y, or I, which are relatively expensive to obtain, and thus is an impractical method for purification of useful quantities of Toxin A.

Production of polyclonal antibodies to Toxin A is known in the art. For example, Ehrich et al., *Inf. Immun.* 28: 1041–43 (1980) teaches a procedure of culturing *C. difficile* and inoculating rabbits to produce polyclonal antibodies to an impure *C. difficile* preparation. Such polyclonal antibodies are not mono-specific for toxin because of the large number of proteins present in culture supernatant. Thus, the performance of toxin specific polyclonal based EIA have been disappointing because of the relatively low toxin specific titer and the high level of nonspecific reactivity of the polyclonal antisera.

Therefore there is a need for a method for the purification of Toxin A as well as a rapid and accurate assay for diagnosis and detection of *C. difficile* Toxin A.

It can be seen by the above that a method for purifying Toxin A which results in a consistently pure and non-denatured protein and which can be used to purify large quantities of protein is needed. Antibodies produced by such a highly purified, active protein will themselves be of higher activity.

SUMMARY OF THE INVENTION

The present invention is drawn to a method for the purification of Toxin A from *Clostridium difficile*. Substantially purified Toxin A is provided which is useful for the production of antibodies to Toxin A. Thus, the invention is also drawn to antibodies, particularly polyclonal antibodies with a high sensitivity for Toxin A. Kits for the diagnosis and detection of *C. difficile* Toxin A are also disclosed. Additional objects, advantages and novel features of the invention will be set forth in part in the description which follows, and in part will become apparent to those skilled in the art upon examination of the following or may be learned by practice of the invention. The objects and advantages of the invention may be realized and obtained by means of the instrumentalities and combinations particularly pointed out in the appended claims.

BRIEF DESCRIPTION OF THE DRAWINGS

Many aspects of the invention can be better understood with reference to the following drawings.

FIG. 1 is a comparison graph of the two curves generated by the data given in Table 1, illustrating that the dose-response curves were equivalent to each other, indicating that the two *C. difficile* Toxin A antigen preparations are comparable in reactivity.

FIG. 2 is a comparison graph of the data in Table 5, which clearly shows the difference in sensitivity between the antibodies of the present invention and those of the prior art.

FIG. 3 is a chart of test data was collected for nine lots of antibodies prepared according to methods of the present invention. The data show that the method of the present invention for producing the antibodies is fairly reproducible with endpoint titers typically of 1:640K.

DETAILED DESCRIPTION

Compositions and methods for the detection of pseudomembranous colitis caused by *C. difficile* are provided. Specifically, a new method for purification and production of Toxin A is disclosed. Further, polyclonal antibodies are provided which are specific for Toxin A of *C. difficile*. The antibodies find use in assays for the detection and diagnosis of *C. difficile*.

DEFINITIONS

The term "substantially pure" or "purified Toxin A" as used herein indicates that the Toxin A preparation is substantially free of contaminating substances when examined by resolving techniques known in the art.

The term "partially pure" or "partially purified Toxin A" refers to Toxin A preparations having some, but not all, contaminants removed.

The term "active Toxin A" refers to Toxin A which gives a positive result on Toxin A assays currently used in the field including ELISA's and the Latex Agglutination Test which uses purified rabbit anti-*C. difficile* antibody immobilized onto Latex beads.

The term "denatured" refers to protein or more specifically, Toxin A, which has lost its native or natural structure or properties.

The term "mono-specific antibody for Toxin A" refers to an antibody which does not have any determinant sites for antigens of *C. difficile* other than Toxin A.

DESCRIPTION

The present invention comprises a highly reproducible method for purifying Toxin A having high activity. The reproducibility of the present process is a very desirable feature of protein purification processes in general and especially for the purification of proteins to be used as antigens. The more pure a preparation of antigen is, the more specific the antibodies produced will be towards that antigen. In addition, reproducibility is of high priority for processes involved in the preparation of products submitted for Food and Drug Administration (FDA) approval.

Toxin A is produced by *C. difficile* cells which may be cultured as is known in the art. The following references describe the culturing of *C. difficile* and are incorporated herein by reference: Sterne and Wentzel, *J. Immun.* 65: 175–183 (1950); Ehrich et al., *Infect. Immun.* 28: 1041–43 (1980); Sullivan et al., *Infect. Immun.* 35: 1032–40. The present invention comprises reversibly binding the crude or partially purified Toxin A to immobilized polyclonal antibody. Polyclonal antibodies are oxidized and are then bound or immobilized to a hydrazide group containing resin, such as hydrazide activated agarose gel. The resulting immobilized reagent is highly selective for Toxin A and its use as a purification reagent results in a highly purified Toxin A. The purification process is much more reproducible than processes using precipitation because the immune-affinity step is very selective for Toxin A and the protein product is of consistent composition, namely highly pure and highly active Toxin A. Also, multiple potentially denaturing washing and resuspension steps are not necessary. In addition, the process of selectively binding and eluting Toxin A to the resin does not permanently denature or inactivate the Toxin A. Therefore, more active mono-specific, polyclonal antibodies may be produced by using the purified, highly active, Toxin A of the present invention.

The process of the present invention is more economical than prior art immuno-affinity processes because the immuno-affinity resin is stable and reusable for many uses. The resin materials are fairly inexpensive and the immuno-affinity resin has a high binding capacity because it presents to the Toxin A containing solution two Toxin A binding sites per bound antibody molecule.

The purification method of the present invention involves an immuno-affinity purification. After elution and re-naturation, the Toxin A is a non-denatured or inactivated protein due to the purification process of selectively binding to and eluting the purified Toxin A antigen from the immobilized anti-Toxin A antibody hydrazide resin. An advantage of the immuno-affinity purification is that the protein is not subjected to centrifugation/rehydration steps during the procedure. The process is thus controlled and very reproducible, and results in consistently pure, non-denatured Toxin A antigen.

The purification method provides purified toxin which maintains the native conformation of the toxin. The elution buffer provides the stability necessary to stabilize the tertiary structure of the Toxin A. Toxin A is speculated to be a large single- or diprotomer with several repeating domains at the —COOH terminus. For this reason, renaturation of the protein is extremely difficult. The purification method addresses this problem with elution in a buffer comprising Tween 20. As a result, the purification method maintains the integrity of the protein during purification which is critical for its use in antibody production.

Culture filtrate of *Clostridium difficile* can be applied directly to an immuno-affinity column as described herein. Alternatively, additional steps for purification of the Toxin A prior to application to the immuno-affinity column may be performed. Such steps include high speed centrifugation followed by filtration, precipitation such as ammonium sulfate precipitation, and chromatography such as ion exchange, or size exclusion chromatography.

The immuno-affinity columns of the present invention utilize hydrazide activated agarose. That is, the antibodies specific to Toxin A are immobilized onto hydrazide activated agarose through the oxidized oligosaccharides of the Fe domain of the IgG antibody molecule. Such methods are known in the art. See, e.g., O'Shannessy and Wilchek, *Anal. Biochem.* 191: 1–8 (1990); Domen et al., *J. Chromat.*, 510:293–302 (1990); Palmer et al., *J. Biol. Chem.* 238: 2393 (1963); Schneider et al., *J. Bio. Chem.* 257: 10766 (1982); all of which references are incorporated by reference herein.

The use of hydrazide group containing resins for biomolecule purification is a known technique. See O'Shannessy and Wilchek supra. Commercial preparations are available wherein agarose beads are provided with spacer arms having terminal hydrazide groups. These hydrazide groups will react with aldehyde groups such as are produced by the oxidation of carbohydrate groups.

Carbohydrate groups are located primarily in the Fe region on antibody molecules. The antigen binding sites are, on the other hand, located on the Fab region of the antibody. Thus, antibodies bound to a hydrazide group containing resin are oriented so that both of their antigen binding sites are presented to antigens such that these immuno-affinity resins may function as better affinity materials. In addition, the long spacer arms of such hydrazide-agarose gels appear to allow for higher binding capacity for antigen, as compared to other types of antibody-resins.

When monoclonal antibodies elicited to acetate precipitated Toxin A are compared with antibodies elicited to immuno-affinity purified Toxin A, using the purified antibodies immobilized onto latex in the LAT, an average endpoint of approximately 25–35 ng/ml is found with the monoclonal antibodies from acetate precipitated Toxin A while an average endpoint in the range of about 12.5–25 ng/ml is found for the antibodies from the immuno-affinity purified Toxin A.

The LAT is a more tightly controlled assay than the ELISA and gives more consistent results. The LAT can be carried out as described in U.S. Pat. Nos. 4,879,218 and 5,098,826 to Wilkins et al., and also as described in Lyerly et al., *J. Clin. Micro,* 21: 12–14 (1985), the disclosures of which are incorporated herein by reference.

Purified Toxin A is useful in studying diseases caused by *C. difficile* and in designing detection tests and treatment plans. In particular, purified Toxin A is necessary for preparing antibodies to Toxin A, which antibodies are used in ELISAs, LATs, and other detection tests such as those described in the above-cited references for detecting the presence of Toxin A in biological samples. In the development of any immunoassay, the first consideration is the quality of the antibody that will be used in the assay. If the antibody is not sensitive or has cross reactivities with other undesired or related proteins, the assay will not have the desired sensitivity and specificity. Thirty (30) or more proteins expressed by *C. difficile* are present in the culture supernatant. Any of these proteins which are present in the final Toxin A antigen product will diminish the efficiency of the antigen used as an immunogen. A purer antigen will generally result in a more specific antibody. Therefore, an improved method for purifying Toxin A antigen is needed which provides highly purified, non-denatured, Toxin A.

Mono-specific antibodies can be produced in accordance to the present invention by immunizing appropriate animals with Toxin A purified as disclosed herein. It is also anticipated that monoclonal antibodies can be prepared using the Toxin A of the present invention. Mono-specific polyclonal antibodies show high activity in ELISA tests and in the LAT. Antibodies raised against Toxin A of the present invention were up to twice as active in the LAT as monoclonal antibodies raised against acetate precipitated Toxin A. In particular, the present antibodies have an average endpoint of about 10 ng/ml–25 ng/ml. Thus, the antibodies of the present invention exhibit a minimum sensitivity greater than that prepared by, for example, Wilkins et al. 's monoclonal antibodies raised to acetate precipitated Toxin A as described in the patents listed above, with an average endpoint of approximately 25 ng/ml–35 ng/ml.

In a second embodiment of the invention, polyclonal antibodies can be produced with the purified, highly active Toxin A through methods known in the art. For example, the methods taught by Ehrich et al., *Infect. Immun.,* 28: 1041–43 (1980) and in E. Harlow & D. Lane, *Antibodies—A Laboratory Manual,* Cold Spring Harbor Laboratory (1988), may be used. The initial step is the preparation of a toxoid and immunization of rabbits with the toxoid. Toxin A-adjuvant is then prepared and used for immunization. The collected sera is then purified over protein A.

The above described production and purification of *C. difficile* Toxin A, and its use in preparing antibodies, are illustrated by the following example, which is not intended to be limiting.

ASSAYING

Protein Purification

*C. difficile* was cultured in 0.85% sodium chloride in dialysis bags suspended in brain-heart infusion (BHI) broth media as generally described by Sterne et al., *J. Immun.,* 65: 175–183 (1950) and Lyerly et al., *J. Clin. Micro.* 17: 72–78 (1983) (incorporated herein). Five dialysis bags holding 300–500 ml each of 0.85% NaCl were placed in 15L of BHI broth media in a 20L Bellco Spinner flask. Each tube was inoculated with 3 ml of a 18–24 hr culture diluted 1:10 with 0.85% chloride. The cells were cultured anaerobically for about four days at 39° C. +/−1° C. After sedimenting the cells by centrifugation at 10,000 RCF for 30 minutes at 2–8° C., the supernatant was decanted off and clarified by filtration through a 0.45 micron filter.

The culture supernatant was concentrated and washed using an apparatus such as the Minitan Ultrafiltration System with PTHK 100,000 MW packet type ultrafiltration membranes. The supernatant was washed with 50 mM Tris buffer, pH 7.5 containing 0.02% sodium azide using twice the starting volume of the filtered culture supernatant. After washing, the washed culture supernatant was concentrated to approximately 250–300 ml.

The washed and concentrated culture supernatant was next subjected to ion-exchange chromatography. An ion-exchange resin which works well is DEAE-Sepharose. A 300–400 ml column was equilibrated in 50 mM Tris buffer pH, 7.5, 50 mM NaCl, at 2–8° C. The Toxin A containing solution was loaded onto the column whereupon the Toxin A was retained. Proteins were then eluted using a gradient from 50–250 mM NaCl while the eluant was monitored at 280 nm. Those fractions having an absorbance greater than 0.05 AUFS were subjected to crossed IEP with the fractions run in one dimension and a reference anti-Toxin A antibody in the second dimension. Crude Toxin A fractions were pooled and collected. These fractions can be stored for one week at 2–8° C. or longer at −20° C.

Immuno-Affinity Column

The immuno-affinity separation column is prepared generally according to the method taught by Pierce Chemical in its 1989 product information brochure on its CarboLink™ Gel. 20 mg of affinity purified anti-Toxin A antibody was oxidized with an equivalent weight amount of sodium meta-periodate by incubating the one to one combination at room temperature for 60 minutes. The mixture was then applied to a 1.6×20 cm Sephadex G-25 column equilibrated and run with 0.1 M NaPi, pH 7.0. The eluant was monitored at 280 nm and the protein-containing fractions were pooled.

20 ml hydrazide group containing agarose beads, sold under the trademark "CarboLink" by Pierce Chemical, were washed with the same buffer and then combined with the oxidized antibody. The mixture was incubated 16–18 hours at room temperature and then packed into a small column (2.5×10 cm) where it was washed with the same buffer. The column was monitored at 280 nm to detect uncoupled antibody protein and was found to couple greater than 95% of the oxidized antibody. The column was washed with 5 bed volumes of deionized water followed by 5 bed volumes of 1 M NaCl and again with 5 bed volumes of deionized water. The column can be equilibrated and stored in 50 mM Tris, pH 7.5 containing 50 mM NaCl and 0.01% sodium azide.

For use, the immuno-affinity column was equilibrated with about 160 ml 50mM Tris, pH 7.5. Partially purified Toxin A off the ion-exchange column can be purified over the immuno-affinity separation column as follows. Based on a Bio-Rad protein assay, 75 mg of the crude Toxin A was applied to the column. The column was washed and run with 50 mM Tris, pH 7.5 while monitoring the column eluant at 280 nm until a peak eluted off the column. The column was washed with 100 mM Glycine, pH 2.7 containing 1% Tween 20, while monitoring the absorbance of the eluant at 280 nm. The purified Toxin A was eluted from the column as one peak and was collected into a container that contained 50 ml of 0.25 M Tris, pH 8.0. The protein concentration of the purified Toxin A was measured using a BCA assay. The protein solution was concentrated using an Amicon concentrator such as the Amicon Single Channel Concentrator Model 8050 with a YM 30 membrane to a concentration of 1.2 mg/ml. The purified Toxin A can be stored at −20° C. for up to one year, or at −70° C. for more than three years.

Column Regeneration

The immuno-affinity column can be reused up to at least 20 times. After the Toxin A is eluted off the column, the column is washed with 100–150 ml of 1 M NaCl followed by 100 ml of 50 mM Tris, pH 7.5. The column is then equilibrated in 50 mM Tris, pH 7.5 containing 0.01% sodium azide and can be stored at 2–8° C. until ready for reuse.

Toxin A Antibodies

Preparation of antibodies to Toxin A was carried out generally by the method of Enrich el al., *Infect. & Immun.* 28, 1041–1043 (1980) (incorporated herein). Due to the toxicity of the purified Toxin A to rabbits, rabbits cannot be immunized initially with the purified Toxin A but rather must be immunized initially with a toxoid of Toxin A. A "toxoid" is a toxin treated so as to destroy its toxicity but leave it capable of inducing the formation of antibodies on injection. A toxoid was prepared by mixing the Toxin A as purified off the immuno-affinity column with formaldehyde. One ml of 1.2 mg/ml of Toxin A was diluted with 5 ml of sterile saline. One ml of 37% formaldehyde was diluted with 8.25 ml of sterile saline. 6 ml of the prepared 4% formaldehyde solution was added to the diluted Toxin A and the mixture incubated in a 37° C. +/−2° C. water bath for 18 to 24 hours. The toxoid-Toxin A solution was mixed with an equal volume of Freund's adjuvant and this solution was used to immunize rabbits. Freund's complete adjuvant was used for the first two injections and Freund's incomplete adjuvant used thereafter. An immunization schedule as shown in Table 1 was used for toxoid immunization. A fresh toxoid should be prepared the day before each immunization. Once the emulsion of Toxoid and Freund's adjuvant is prepared, it should be injected within two hours.

TABLE 1

| Immunization Number | Amount (ml) per Rabbit | Route: (0.5 ml per Two Sites) | Day of the Schedule |
| --- | --- | --- | --- |
| 1 | 1.0 | POP* | 1 |
| 2 | 1.0 | POP | 3 |
| 3 | 1.0 | POP | 8 |
| 4 | 1.0 | POP | 10 |
| 5 | 1.0 | POP | 15 |
| 6 | 1.0 | POP | 17 |
| 7 | 1.0 | POP | 22 |
| 8 | 1.0 | POP | 24 |
| 9 | 1.0 | IM* | 29 |
| 10 | 1.0 | IM | 31 |
| Test Bleed | | | 36 |
| 11 (boost) | 1.0 | IM | 40 |
| Test Bleed | | | 44 |

*POP = popitiel
*IM = intramuscular

On day 36 +/−1, 2–3 ml of blood was collected from each rabbit and the anti-Toxin A titer measured using an ELISA assay. An endpoint of greater than or equal to 1:5000 was considered acceptable. If the titer was not acceptable, the rabbits were boosted with another toxoid injection and the titer retested on day 44+/−1.

Once a protective titer against the toxoid of Toxin A has been achieved, the rabbits can be immunized against the purified Toxin A. The Toxin A was diluted to about 0.4 mg/ml with sterile saline. This solution was then diluted to about 0.2 mg/ml with Freund's incomplete adjuvant. Each rabbit was immunized with 1 ml of this solution. Rabbits were immunized according to the immunization schedule of Table 2.

TABLE 2

| Immunization Number | Amount (ml) per Rabbit | Route: (0.5 ml per two sites) | Day of the Schedule |
| --- | --- | --- | --- |
| 1 | 1.0 | IM | 1 |
| 2 | 1.0 | IM | 8 |
| 3 | 1.0 | IM | 15 |
| 4 | 1.0 | IM | 22 |
| Test Bleed | | | |
| 5 (boost) | 1.0 | IM | 30 |
| Test Bleed | | | 35 |

On approximately the 27th day of the immunization schedule, the animals were tested for antibody titer as described above. If the titer was high enough, at about or higher than 1:40,000, the rabbits were bled and the sera collected.

The sera prepared in the foregoing manner was clarified, when necessary, by high speed centrifugation and/or filtration and then precipitated with 70% ammonium sulfate. The precipitated globulin was resuspended in 20 mM NaPi, pH 7.4 and then purified over a protein A column.

Preparation of Latex-Bound Antibodies

For use in a Latex Agglutination Test (LAT) the antibodies are bound to latex using the following procedure. Rabbit polyclonal and mouse monoclonal anti-*C. difficile* Toxin A antibodies were prepared and dialyzed into 20 mM NaPi, pH 6.0 with 0.01% sodium azide. The protein concentration of the solution was adjusted to about 2.0 mg/ml. 50 ml of 2.5% (w/v) solids carboxylated polystyrene latex was placed into each of four 250 ml centrifuge bottles. 70 ml of 20 mM NaPi, pH 6.0 was added to each bottle and the bottles centrifuged at 11,000 RCF for 30–40 minutes. The liquid was poured off and the beads were resuspended in 120 ml of the same buffer. For latex suspensions, the latex must be resuspended initially in a minimal volume of buffer. The bottles were centrifuged as before and the washing step was repeated. The beads were then resuspended in 120 ml of the same buffer and 50 mg of 1-ethyl -3-[3-dimethyl aminopropyl]-carbodiimide hydrochloride and 12.5 mg sulfo-N-hydroxysuccinimide was added to each bottle. The latex suspensions were allowed to incubate for two hours at room temperature while stirring. The suspension was pelleted by centrifugation at 11,000 RCF for 30–40 minutes, the supernatant poured off, and each pellet resuspended in 120 ml of 20 mM NaPi, pH 6.0. The suspension was pelleted as before and this step was repeated. 15 mg of the buffer exchanged antibodies were added to each latex suspension and the resulting latex-antibodies suspension incubated for 18–20 hours at room temperature while stirring. 2.5 ml of 1M 2-aminoethanol was added to each suspension and the resulting solution incubated for two hours at room temperature while stirring. The latex-antibodies suspension was then pelleted at 10,000 RCF for 30–40 minutes, the supernatant decanted and each pellet resuspended in 250 ml of 0.1 M glycine-NaOH, pH 8.2 with 0.15 M sodium chloride, 0.25% Tween 20, 0.2% sodium azide, and 0.2% BSA. The latex-antibodies were pelleted at 10,000 RCF for 30–40 minutes and this step repeated.

LAT

A volume of Toxin A containing solution was mixed with 0.5 ml specimen buffer in a centrifuge tube and vortexed for 30 seconds. The tube was then centrifuged for 15 minutes at a minimum of 1500×g. Using a typical LAT test card, 35 μl of the specimen supernatant was placed in the test circle and 35 μl in the negative circle of the test card. 35 μl of a *C. difficile* culture filtrate was placed in the positive circle. 35 μl of the Toxin A coated latex beads were placed in the test and positive circles. 35 μl of normal rabbit antibody coated latex beads was placed in the negative circle. The contents of each circle were mixed with a separate applicator stick and spread over the surface of each circle. Using a clinical rotator, the test card was rotated for the designated time at 100 rpm. The test was read microscopically under a fluorescent light.

Activity of Antibodies

Table 3 shows the results of a comparison of monoclonal antibodies raised against acetate precipitated Toxin A with antibodies raised against immuno-affinity purified Toxin A. The antibodies raised against immuno-affinity purified Toxin A were prepared according to the description recited above. After the rest period, the rabbits were bled every two weeks and the bleeds were purified as described above and coupled to latex beads as described above. The LAT procedure described above was used to compare the antibodies.

As can be seen from the data, antibodies prepared in accordance with the present invention and used in the Latex Agglutination Test gave results of an average endpoint of 12.5–25 ng/ml. Monoclonal antibodies prepared using acetate precipitation gave results of an average endpoint of 25–35 ng/ml.

TABLE 3

| Monoclonal antibodies raised against acetate precipitated Toxin A | | | | | | | | |
|---|---|---|---|---|---|---|---|---|
| Toxin A | Bleed Date 10/03 | | Bleed Date 12/07 | | Bleed Date 2/22 | | Bleed Date 3/22 | |
| Conc. (ng/ml) | 2 min. | 4 min. | 2 min. | 4 min. | 2 min. | 4 min. | 2 min. | 4 min. |
| 200 | 3+ | 4+ | 4+ | 4+ | 4+ | 4+ | 4+ | 4+ |
| 100 | 2+ | 3+ | 3+ | 4+ | 2+ | 4+ | 3+ | 4+ |
| 50 | 1+ | 2+ | 2+ | 3+ | 1+ | 3+ | 2+ | 3+ |
| 35 | <1+ | 1+ | 1+ | 2+ | Vague | 1+ | <1+ | 1+ |
| 25 | Neg. | Neg. | Vague | 1+ | Neg. | <1+ | Neg. | Neg. |
| 12.5 | Neg. | Neg. | Neg. | Vague | Neg. | Vague | Neg. | Neg. |
| 6.25 | Neg. | Neg. | Neg. | Neg. | Neg. | Neg. | Neg. | Neg. |
| Antibodies raised, against immuno-affinity purified Toxin A | | | | | | | | |
| Toxin A | Bleed Date 1/04 | | Bleed Date 3/14 | | Bleed Date 4/11 | | Bleed Date 5/24 | |
| Conc. (ng/ml) | 2 min. | 4 min. | 2 min. | 4 min. | 2 min. | 4 min. | 2 min. | 4 min. |
| 200 | 4+ | 4+ | 44− | 4+ | 4+ | 4+ | 4+ | 4+ |
| 100 | 4+ | 4+ | 4+ | 4+ | 4+ | 4+ | 3+ | 4+ |
| 50 | 4+ | 4+ | 3+ | 4+ | 3+ | 4+ | Vague | 2+ |
| 35 | 3+ | 4− | 1+ | 3+ | Vague | 3+ | <1+ | 1+ |

TABLE 3-continued

| 25 | 1 | 2+ | Vague | 1+ | Neg. | <1+ | Neg. | Neg. |
| 12.5 | Vague | 1+ | Neg. | Vague | Neg. | Neg. | Neg. | Neg. |
| 6.25 | Neg. | <1+ | Neg. | Neg. | Neg. | Neg. | Neg. | Neg. |

Another test was performed, and results show that the Rabbit anti-*C. difficile* Toxin A antibody (Pab), prepared according to the present invention, has greater sensitivity as compared with the monoclonal anti-*C. difficile* Toxin A antibody (Mab), when compared in a sandwich ELISA format. In the ELISA assay described here, separate microwells were coated with the Pab and the Mab. The ELISA assay procedure is given below. The Pab is compared with the Mab patented by Wilkins et al. from the PCG-4 cell clone since the existing antibody patent to Wilkins et al covers the application of the Mab antibody for use as both a detection and a capture antibody for the quantitation of the Toxin A protein in a two-site immuno-assay using the Mab antibody.

The ELISA procedure, which was used to generate Tables 4 and 5 below and FIGS. 1 and 2, is as follows. Immulon™4 plates were coated with 100 μl of each antibody solution at 1:20,000 dilutions in 0.05M carbonate buffer pH 9.6 and incubated for 16–18 hours at 2–8° C. It should be noted that the protein concentration of the well coating solutions for both antibodies were at 5.0 ng/well based on initial protein concentration of 1.0 mg/ml. The following day each well of the plate was washed five times with the wash buffer and blocked with 200 μl blocking buffer followed by an incubation at 37° C. for 30 minutes. The *C. difficile* Toxin A samples were diluted in phospho-saline (PBS) buffer and 100 μl of each diluted sample was run in respective wells.

The ELISA plate containing the samples was incubated for 60 minutes at room temperature followed by a 5×wash with wash buffer. Goat anti-*C. difficile* Toxin A antiserum was diluted to 1:5000 in a PBS buffer and 100 μl of the diluted antiserum was added per well and incubated for 60 minutes at room temperature followed by a 5×wash with wash buffer. Rabbit anti-Goat HRP conjugate was diluted to 1:40,000 in PBS buffer and 100 μl of the diluted conjugate was added per well and incubated for 60 minutes at room temperature followed by a 5×wash with wash buffer. 100μl of the working substrate was added to each well and allowed to incubate at room temperature for 5 minutes at room temperature. After the development of color in the wells, 100 μl of stop solution (1M phosphoric acid) was added. Each well of the ELISA plate was read at 450 nm.

In Assay Number 1, the Wilkins et al. purified Toxin A was tested in parallel with the purified Toxin A of the present invention. The results show that the two toxins used for immunization for the preparation of either the Pab by the procedure of the present invention or the Mab by the Wilkins et al procedure are essentially the same in terms of reactivity. This is clearly shown in Table 1 and FIG. 1.

It should be noted that in Assay Number 1, the two *C. difficile* Toxin A antigens were tested in parallel to show that the reactivity of the two antigens are comparable. The rabbit anti-*C. difficile* Toxin A affinity purified antibody of the present invention was used as the capture antibody. The goat anti-*C. difficile* Toxin A antiserum was used as the signal antibody.

TABLE 4

| Purified Toxin A Concentration (ng/ml) | Toxin A Ag of present invention Blank Corrected O.D. at 450 nm (AA) | Toxin A Ag of Wilkins et al Blank Corrected O.D. at 450 nm (BB) | % Ratio O.D. of AA to BB |
| --- | --- | --- | --- |
| 78 | 1.493 | 1.412 | 105.74 |
| 39 | 0.891 | 0.881 | 101.08 |
| 19.5 | 0.506 | 0.483 | 104.87 |
| 9.75 | 0.260 | 0.245 | 106.12 |
| 4.9 | 0.091 | 0.090 | 101.11 |
| 2.4 | 0.040 | 0.042 | 95.26 |
| | | | Average = 102.36 |

As can be observed from Table 1 and FIG. 1, the dose-response curves were equivalent to each other indicating that the two *C. difficile* Toxin A antigen preparations are comparable in reactivity. See FIG. 1 for the graphic comparison of the two curves generated by the data given in Table 1 above. This is significant since it is known that monoclonal antibodies typically react only with one or two epitopes while a typical polyclonal antibody will react with multiple epitopes, thus allowing for greater sensitivity. The polyclonal antibodies of the present invention were tested against the specified monoclonal antibodies because the monoclonal antibodies are the antibodies typically used in the prior art for comparison with the antibodies of the present invention.

In this instance, the Toxin A molecule is a large 308 kDalton molecular weight, that is speculated to be a one or two subunit protein with multiple domains containing several epitopes per domain.

In Assay Number 2, the mouse anti-*C. difficile* Toxin A antibody is tested in parallel with the rabbit anti-*C. difficile* antibody of the present invention. The purpose of the assay is to show that the minimum sensitivity of the Pab of the present invention is greater than that of the Mab.

In Assay Number 2, the Mab and Pab of the present invention were compared in parallel with the purified *C. difficile* Toxin A antigen. The ELISA results for the purified Toxin A are given in Table 2. As can be observed, the Pab gives a positive signal to noise ratio at 0.24 ng with an estimated minimum sensitivity of 0.22 ng. For the Mab, the minimum sensitivity is estimated at 0.975 for this assay.

TABLE 5

| Purified Toxin A Concentration (ng/ml) | Amount of purified Toxin A per well based on 0.1 ml sample size (ng/well) | Pab O.D. at 450 nm Blank Corrected | Mab O.D. at 450 nm Blank Corrected |
| --- | --- | --- | --- |
| 78 | 7.8 | 1.028 | 0.486 |
| 39 | 3.9 | 0.700 | 0.342 |
| 19.5 | 1.95 | 0.427 | 0.145 |
| 9.75 | 0.975 | 0.221 | 0.061 |
| 4.9 | 0.49 | 0.104 | −0.002 |
| 2.4 | 0.24 | 0.035 | 0.011 |

The data in Table 5, presented graphically in FIG. 2, clearly show the difference in sensitivity between the two antibodies. It can be determined that the antibody that was raised against an antigen from the purification process of the present specification results in an assay with better sensitivity as compared with the Mab. Therefore, the affinity purified Pab of the present invention is superior for use as a detection or capture antibody. Additionally, affinity purified Pab could be used in the detection system of a *C. difficile* Toxin A antigen assay by chemically coupling the antibody to an enzyme, fluorescent dye, immuno-gold or colored liposome.

Multiple reproducible lots of the antibody can be produced using the methods described herein. As can be seen from the Table 6 below and FIG. 3, test data were collected for nine lots. The data are fairly reproducible with endpoint titers typically of 1:640K. The data are expressed as an endpoint titer comparing a reference and test antibody in an ELISA format. The "endpoint titer" is defined as the highest dilution of antibody (test or reference) which results in an absorbance value greater than the average blank absorbance value. In the ELISA format decreasing amounts of antibody are exposed to a constant amount of purified *C. difficile* toxin A antigen.

Details of the ELISA are as follows. Each ELISA well is initially coated with a coating solution of 60 ng/ml of the purified toxin A. After the plate is coated, it is blocked with a buffer-protein solution which prevents nonspecific binding of the antibody to the plastic walls of the micro-well surface. The initial protein concentration of the antibody being tested is 2.7–3.0 mg/ml as calculated by the absorbance at 280 nm of the antibody solution.

The final protein concentration is Absorbance at 280/1.4× Dilution Factor. A dilution series of each antibody for testing is prepared with the final amounts of antibody equating to the following as shown in FIG. 3: 1:160,000=17.5 ng/ml; 1:320,000=8.75 ng/ml; and 1:640,000=4.38 ng/ml.

TABLE 6

| | Test Lot No. | Reference Lot No. | Endpoint ELISA Titer Test Lot | Endpoint ELISA Titer Refer. Lot |
|---|---|---|---|---|
| Test 1 | 1 | 1 | 1:640 K | 1:640 K |
| Test 2 | 2 | 1 | 1:640 K | 1:640 K |
| Test 3 | 3 | 1 | 1:640 K | 1:640 K |
| Test 4 | 4 | 1 | 1:640 K | 1:640 K |
| Test 5 | 5 | 1 | 1:640 K | 1:640 K |
| Test 6 | 6 | 2 | 1:320 K | 1:320 K |
| Test 7 | 7 | 3 | 1:640 K | 1:640 K |
| Test 8 | 8 | 4 | 1:640 K | 1:640 K |
| Test 9 | 9 | 5 | 1:640 K | 1:320 K |

Lots of the affinity purified *C. difficile* Toxin A antibody made according to the method of the present invention can be used in the successful production of a test kit for the quantitation of *C. difficile* Toxin A from patient specimens. The ELISA test method described above is a valid analytical test method for insuring the efficacy and utility of the antibody product of the present invention.

The foregoing description of preferred embodiments of the invention has been presented for purposes of illustration and description. It is not intended to be exhaustive or to limit the invention to the precise forms disclosed, and obviously many modifications and variations are possible in light of the above teaching. It is intended that the scope of the invention be defined by the claims appended hereto.

The invention claimed is:

1. A method for detecting the presence of *C. difficile* Toxin A in a patient comprising:

coupling Toxin A antibodies to a hydrazide group containing resin;

contacting a solution containing Toxin A with said resin so that said Toxin A is selectively retained on said coupled antibody resin;

eluting purified Toxin A from said antibody resin with Tween 20;

immunizing a host with said purified Toxin A collecting a sample from said host;

isolating and purifying mono-specific polyclonal antibodies for *Clostridium difficile* Toxin A from said sample;

combining said mono-specific polyclonal antibodies with latex particles in a manner whereby the polyclonal antibodies bind the latex particles;

contacting a sample from said patient with the latex particles containing the polyclonal antibodies; and observing the presence or absence of agglutination, wherein the presence of agglutination indicates the presence of *C. difficile* Toxin A.

2. The method of claim 1, wherein the hydrazide group containing resin comprises hydrazide activated agarose.

3. The method of claim 1, wherein the polyclonal antibodies exhibit minimum sensitivity greater than that of a mouse monoclonal anti-Toxin A antibodies for *Clostridium difficile* Toxin A from the PCG-4 cell clone.

* * * * *